(12) United States Patent
Fifolt

(10) Patent No.: US 10,022,174 B2
(45) Date of Patent: Jul. 17, 2018

(54) METHODS AND DEVICES FOR SURGICAL GUIDE PIN PLACEMENT

(75) Inventor: Douglas A. Fifolt, Wrentham, MA (US)

(73) Assignee: DEPUY MITEK, LLC, Raynham, MA (US)

( * ) Notice: Subject to any disclaimer, the term of this patent is extended or adjusted under 35 U.S.C. 154(b) by 1255 days.

(21) Appl. No.: 13/487,880

(22) Filed: Jun. 4, 2012

(65) Prior Publication Data

US 2013/0325124 A1 Dec. 5, 2013

(51) Int. Cl.
| | |
|---|---|
| *A61B 17/16* | (2006.01) |
| *A61B 17/17* | (2006.01) |
| *A61B 17/88* | (2006.01) |
| *A61B 17/56* | (2006.01) |

(52) U.S. Cl.
CPC ...... *A61B 17/8897* (2013.01); *A61B 17/1675* (2013.01); *A61B 17/1714* (2013.01); *A61B 17/1764* (2013.01); *A61B 2017/564* (2013.01)

(58) Field of Classification Search
USPC .................. 623/13.11–13.14; 606/88, 96–98
See application file for complete search history.

(56) References Cited

U.S. PATENT DOCUMENTS

| | | | | |
|---|---|---|---|---|
| 4,535,768 | A * | 8/1985 | Hourahane et al. ........ | 606/86 R |
| 5,152,766 | A * | 10/1992 | Kirkley .......................... | 606/103 |
| 5,234,435 | A * | 8/1993 | Seagrave, Jr. ................ | 606/103 |
| 5,643,273 | A * | 7/1997 | Clark .............................. | 606/96 |
| 5,895,425 | A * | 4/1999 | Grafton et al. ............... | 606/304 |
| 6,371,124 | B1 * | 4/2002 | Whelan ........................ | 128/898 |
| 6,499,486 | B1 * | 12/2002 | Chervitz et al. ............. | 128/898 |
| 6,733,529 | B2 * | 5/2004 | Whelan ...................... | 623/13.12 |
| 7,637,910 | B2 | 12/2009 | Schmieding et al. | |
| 8,388,621 | B2 * | 3/2013 | Bourque et al. ............... | 606/80 |
| 2002/0055714 | A1 * | 5/2002 | Rothschild ................. | 604/164.1 |
| 2004/0254585 | A1 | 12/2004 | Whittaker et al. | |
| 2007/0233151 | A1 * | 10/2007 | Chudik ........................... | 606/96 |
| 2008/0161864 | A1 | 7/2008 | Beck et al. | |
| 2009/0228013 | A1 * | 9/2009 | Bourque et al. ............... | 606/80 |
| 2011/0208194 | A1 * | 8/2011 | Steiner et al. .................. | 606/80 |
| 2012/0197395 | A1 * | 8/2012 | Berg .......................... | 623/13.14 |
| 2012/0197396 | A1 * | 8/2012 | Berg .......................... | 623/13.14 |
| 2013/0158555 | A1 * | 6/2013 | Bourque et al. ............... | 606/80 |

FOREIGN PATENT DOCUMENTS

EP 2 286 742 A1 2/2011

* cited by examiner

*Primary Examiner* — Zade Coley

(57) ABSTRACT

Methods and devices are provided for placing surgical guide pins, reamers, and ligament grafts into bone. In one exemplary embodiment, the method can include advancing a guide pin that includes a proximal rigid portion and a flexible distal portion. The rigid proximal portion can be advanced into a femoral tunnel such that the flexible distal portion extends across an intra-articular space. The flexible portion of the guide pin can be bent to adjust a distance between the guide pin and articular cartilage. A cannulated reamer can be advanced over the flexible portion of the guide pin and the reamer can be manipulated to avoid contact with the articular cartilage in the intra-articular space. A ligament graft can be secured in the femoral tunnel created by the guide pin and the reamer.

14 Claims, 6 Drawing Sheets

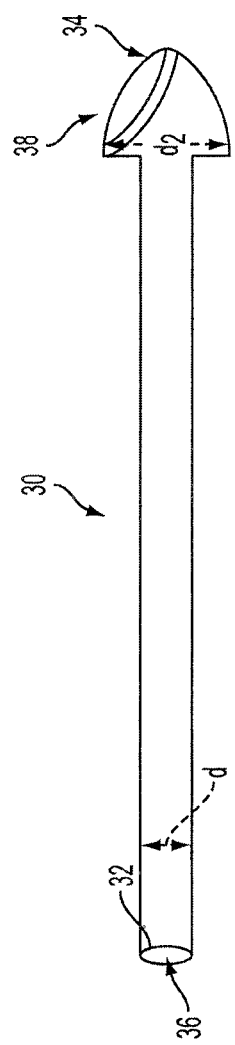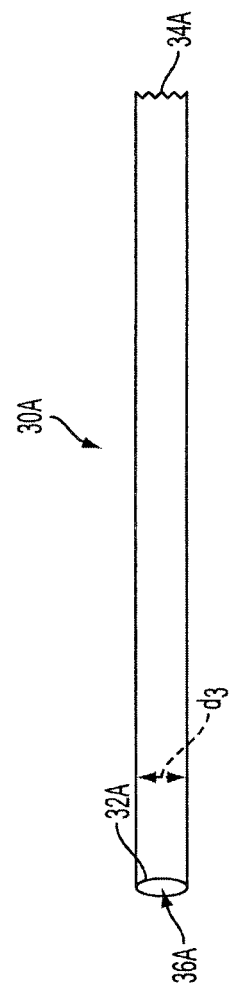

METHODS AND DEVICES FOR SURGICAL GUIDE PIN PLACEMENT

FIELD OF THE INVENTION

The present invention relates generally to methods and devices for surgical guide pin placement, and in particular to placing guide pins in performing soft tissue repair.

BACKGROUND OF THE INVENTION

Joint injuries may commonly result in the complete or partial detachment of ligaments, tendons and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. A number of conventional surgical procedures exist for re-attaching such tendons and ligaments to bone.

One such procedure involves the re-attachment of the detached tissue using "traditional" attachment devices such as staples, sutures, and bone screws. Such traditional attachment devices have also been used to attach tendon or ligament grafts (often formed from autologous tissue harvested from elsewhere in the body) to the desired bone or bones. In one procedure, a damaged anterior cruciate ligament ("ACL") is replaced by a ligament graft in a human knee.

Two popular approaches to ACL reconstruction include a transtibial approach and an anteromedial approach. In the transtibial approach, a surgeon will first drill a tunnel through a tibia and insert a guide pin through the tunnel and through intra-articular space between a femur and the tibia to locate and drill an aligned femoral tunnel. Once the guide pin is placed, a reamer overdrills the guide pin and passes into the femur to create a final diameter of the femoral tunnel in which a ligament graft can be positioned and secured. The ligament graft is ultimately secured to the tibia using the tibial tunnel to complete the repair. Drilling the tibia can damage and/or weaken the tibia. Additionally, it can be difficult to determine the proper angle to drill through the tibia to achieve the desired anatomic femoral tunnel position, which can increase time of the surgical procedure and/or can dictate the placement of the femoral tunnel away from the desired location.

In the anteromedial approach, a surgeon inserts the guide pin directly into the femur through the intra-articular space, which renders initial drilling of the tibia unnecessary. However, due to the "shallow" angle of approach directly into the femur, the trajectory brings the guide pin much closer to articular cartilage in the intra-articular space than in the transtibial approach. Since generally a reamer has a larger diameter than the guide pin, it can be challenging to place the reamer over the guide pin without scraping or damaging the articular cartilage because of inadequate clearance in the anteromedial approach.

Accordingly, there remains a need for improved methods and devices for surgical guide pin placement.

SUMMARY OF THE INVENTION

In one embodiment, a surgical method is provided that includes advancing a rigid proximal portion of a guide pin through a tissue opening adjacent to a femur, across an intra-articular space, and into a femoral tunnel such that a flexible distal portion of the guide pin extends across the intra-articular space and extends out of the tissue opening. The flexible distal portion of the guide pin can be bent or flexed within the intra-articular space such that the rigid proximal portion of the guide pin extends at a non-zero angle relative to the flexible distal portion. A cannulated reamer can be advanced over the flexible distal portion of the guide pin to position a proximal tip of the reamer in contact with the femur. The cannulated reamer can be manipulated to substantially avoid contact with articular cartilage within the intra-articular space.

The surgical method can include a variety of modifications. For example, bending the flexible distal portion of the guide pin can include bending the flexible distal portion of the guide pin within the intra-articular space away from the articular cartilage. For another example, advancing the rigid proximal portion of the guide pin through the femur can include advancing the rigid proximal portion of the guide pin to protrude through a lateral side of the femur. For yet another example, after advancing the cannulated reamer over the flexible distal portion of the guide pin, the flexible distal portion of the guide pin can be straightened, and the cannulated reamer can be reamed into the femur over the rigid proximal portion of the guide pin. For another example, the method can include attaching a proximal end of the flexible distal portion to a distal end of the rigid proximal portion to form the guide pin. For another example, the rigid proximal portion and the flexible distal portion can be integrally formed.

In another embodiment, a surgical method is provided that includes advancing a rigid proximal portion of a guide pin anteromedially into a femur to thereby position a flexible distal portion of the guide pin within intra-articular space near the femur, flexing the flexible distal portion of the guide pin within the intra-articular space to adjust a distance between the flexible distal portion of the guide pin and femoral articular cartilage, and advancing a reamer over the flexible distal portion of the guide pin to advance the reamer over the rigid proximal portion of the guide pin and into the femur.

In some embodiments, when the proximal portion of the guide pin is advanced anteromedially into the femur, the distal portion of the guide pin can be rigid. Positioning the flexible distal portion of the guide pin within the intra-articular space can include activating a selectively stiffenable material forming at least a portion of the guide pin to make the distal portion of the guide pin flexible. When the selectively stiffenable material is activated, the rigid proximal portion of the guide pin can remain rigid.

The surgical method can vary in any number of ways. Positioning the flexible distal portion of the guide pin within the intra-articular space can include advancing the proximal portion of the guide pin through the femur to extend out a lateral side of the femur until the flexible distal portion of the guide pin attached to the proximal portion of the guide pin is positioned within the intra-articular space. Adjusting the distance between the flexible distal portion of the guide pin and the femoral articular cartilage can include increasing the distance. The guide pin and the reamer can be removed from a tunnel formed in the femur by the reamer, and, after removing the guide pin and the reamer, a graft can be advanced into the tunnel, and the graft can be secured within the tunnel.

In another aspect, a surgical kit is provided that includes a guide pin and a cannulated reamer. The guide pin has a rigid proximal portion and a flexible distal portion. The rigid proximal portion of the guide pin is configured to be advanced through a tissue opening adjacent to a femur, across an intra-articular space, and into a femoral tunnel such that the flexible distal portion of the guide pin extends across the intra-articular space and extends out of the tissue opening. The flexible distal portion of the guide pin is configured to be bent within the intra-articular space such that the rigid proximal portion of the guide pin extends at a non-zero angle relative to the flexible distal portion of the guide pin. The cannulated reamer is configured to be advanced over the flexible distal portion of the guide pin and to extend across the intra-articular space to position a proximal tip of the reamer in contact with the femur.

The guide pin can be formed of a variety of materials. In one embodiment, at least the flexible distal portion of the guide pin can be formed of a selectively stiffenable material. The flexible distal portion of the guide pin and the proximal rigid portion of the guide pin can be formed of the selectively stiffenable material. Alternatively, the flexible distal portion of the guide pin can be formed of the selectively stiffenable material, and the proximal rigid portion of the guide pin can not be formed of the selectively stiffenable material.

The rigid proximal portion and the flexible distal portion can be integrally formed, or the rigid proximal portion and the flexible distal portion can be separate elements. If the rigid proximal portion and the flexible distal portion are separate elements, a proximal end of the flexible distal portion can be configured to attach to a distal end of the rigid proximal portion to form the guide pin.

BRIEF DESCRIPTION OF THE DRAWINGS

The invention will be more fully understood from the following detailed description taken in conjunction with the accompanying drawings, in which:

FIG. 2 is a side view of one embodiment of a reamer;

FIG. 2A is a side view of another embodiment of a reamer;

DETAILED DESCRIPTION OF THE INVENTION

Figure 1:
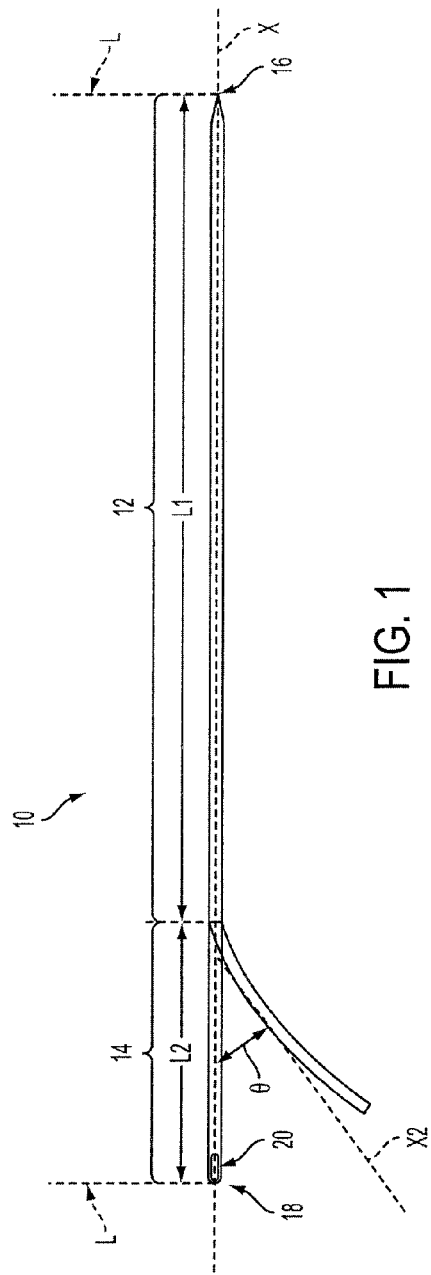
FIG. 1 is a side view of one embodiment of a guide pin.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are disclosed for placing surgical guide pins, such as in an arthroscopic surgical procedure. In general, the methods and devices allow a guide pin to be inserted through intra-articular space into a femur to create a femoral tunnel. In an exemplary embodiment, a guide pin is provided that has a rigid proximal portion and a flexible distal portion configured to be bent or flexed relative to the rigid proximal portion. In other words, the guide pin can include a flexible distal tail. Bending the flexible distal portion when the flexible distal portion is positioned within a patient's body can allow the guide pin to be navigated at a safe distance away from sensitive and/or easily damaged body structures such as cartilage. For non-limiting example, bending the flexible distal portion when the flexible distal portion is positioned within a patient's body near the patient's knee can allow adjustment of a distance between the guide pin and articular cartilage located between the patient's femur and tibia. The guide pin can therefore reduce chances of the guide pin and/or any devices advanced over the guide pin, e.g., a cannulated reamer such as an acorn reamer, contacting, tearing, scraping, or otherwise damaging sensitive and/or easily damaged body structures such as cartilage. Also, the guide pin being configured to flex within intra-articular space can allow a femoral tunnel to be formed in a patient without first drilling a tunnel through the patient's tibia. Since a tibial tunnel need not be formed prior to the femoral tunnel so as to target a location for the femoral tunnel, a more anatomic position can be chosen for the femoral tunnel, which can improve the anatomical accurateness of the repair, and can reduce time and/or complexity of the surgical procedure. Similarly, a tibial tunnel can be formed after the femoral tunnel is formed to finish the repair procedure, but without being tied to targeting a location for the femoral tunnel, a more anatomic position can be chosen for the tibial tunnel.

The guide pins disclosed herein can be formed from any one or more materials, preferably a biocompatible material(s) safe for use in the body, e.g., a polymer, titanium, stainless steel, Nitinol, etc. The guide pin can be formed from one or more materials that allow different portions of the guide pin to have different levels of flexibility. In an exemplary embodiment, a first portion of the guide pin, e.g., a distal portion thereof, can be formed from one or more flexible materials such that the first portion has some degree of elasticity, e.g., can bend without breaking. A second portion of the guide pin, e.g., a proximal portion thereof, can be formed from one or more rigid materials such that the second portion of the guide pin is substantially non-bendable. However, the guide pin can be made from any type of material and any combination of materials able to provide structure to the guide pin as discussed below and as appropriate for use in a body.

In an exemplary embodiment, the guide pin can be formed at least partially from at least one selectively stiffenable material such as a shape memory material, which can include a single material or a combination of materials. Non-limiting examples of shape memory materials include copper-zinc-aluminum-nickel alloys, copper-aluminum-nickel alloys, nickel-titanium alloys such as Nitinol, thermoplastic materials such as Nylon or Nylon blends, and shape memory polymers such as Veriflex™. The selectively stiffenable material can facilitate the guide pin being movable between an elongated configuration, in which the guide pin can have a substantially linear or straight configuration, and a deformed configuration, in which the guide pin can be flexed from the substantially linear or straight configuration. The selectively stiffenable material can also facilitate the guide pin being naturally biased to the elongated configuration, which can facilitate introduction of the guide pin into a patient's body, as discussed further below. In an exemplary embodiment, the entire guide pin can be formed from one or more selectively stiffenable material. In another exemplary embodiment, a distal portion of a guide pin can be formed from one or more selectively stiffenable material, and a proximal portion of the guide pin can be formed from one or more rigid materials.

FIG. 1 illustrates one exemplary embodiment of a guide wire or guide pin 10, generally referred to herein as a "guide pin," configured to traverse the intra-articular space and to extend into a femur. The guide pin 10 can have various sizes, shapes, and configurations. The guide pin 10 can include an elongate member having a substantially cylindrical shape with a substantially circular cross-section, as shown in FIG. 1, although the guide pin 10 can be an elongate member having a different shape and/or different cross-section. In certain embodiments, the cross-sectional shape can vary at certain locations to provide desired stiffness or flexibility. The guide pin 10 can have a substantially constant outer diameter, which can facilitate introduction of the guide pin 10 into tissue and/or bone and advancement of the guide pin 10 through the tissue and/or bone. As discussed further below, proximal and distal ends of the guide pin 10 can have different shapes and/or different outer diameters than a remainder of the guide pin 10.

As illustrated in FIG. 1, the guide pin 10 can include a proximal portion 12 and a distal portion 14 that can be configured to be coaxially aligned along a longitudinal axis X of the guide pin 10. As discussed further below, the distal portion 14 can be configured to bend radially away in any direction from the axis X such that a longitudinal axis of the proximal portion 12 remains coaxial with the pin's axis X while a longitudinal axis X2 of the distal portion 14 is at a non-zero angle θ relative to the pin's axis X. The distal portion 14 is shown in phantom at the non-zero angle θ in FIG. 1. The guide pin 10 can be solid or cannulated.

Figure 1A:
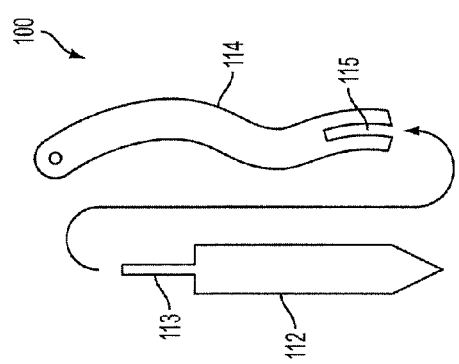
FIG. 1A is a side view of another embodiment of a guide pin.

The proximal and distal portions 12, 14 can be formed unitarily, as illustrated in FIG. 1. Alternatively, proximal and distal portions of a guide pin can be separate components with a proximal end of the distal portion being configured to attach to a distal end of the proximal portion to form the guide pin, such as by compression fit, snap fit, adhesive connection, welding, etc. FIG. 1A illustrates one embodiment of a guide pin 100 including separable proximal and distal portions 112, 114. The proximal portion 112 can include a mating feature 113, e.g., a male member, configured to couple to a mating feature 115, e.g., a female member, of the distal portion 114 to securely affix the proximal portion 112 to the distal portion 114. The mating features 113, 115 in the illustrated embodiment include complementary male and female members, but the mating features can have a variety of configurations, e.g., complementary threads, compression fit members, snap fit members, etc. An adhesive can be applied to the mating features 113, 115 to further help secure the proximal and distal portions 112, 114 together.

Referring again to FIG. 1, the proximal and distal portions 12, 14 can be visually indistinguishable, or the guide pin 10 can include at least one visual indicator configured to visually distinguish between the proximal and distal portions 12, 14. The at least one visual indicator can facilitate flexing of the distal portion 14, as discussed further below. Non-limiting examples of visual indicators include different colors or different shades of colors on the proximal and distal portions 12, 14; different numeric, alphabetic, and/or abstract patterns being printed or otherwise formed on the proximal and distal portions 12, 14; a fluorescent material such that one of the proximal and distal portions 12, 14 can fluoresce when exposed to light having a certain wavelength and/or such that the proximal and distal portions 12, 14 can fluoresce different colors when exposed to lights having different wavelength; etc.

A total longitudinal length L of the guide pin 10 can vary. A proportion between longitudinal lengths L1, L2 of the proximal portion 12 and the distal portion 14, respectively, can vary, but, generally, the proximal portion 14 can have a longitudinal length L1 that is sufficient enough to allow drilling into bone. In an exemplary embodiment, the longitudinal length L1 of the proximal portion 12 can be equal to or greater than the longitudinal length L2 of the distal portion 14. In other words, the proximal portion 12 can form at least half of the guide pin's total longitudinal length L. In this way, a majority of the pin 10 can be rigid, which can facilitate advancement of the pin 10 through tissue and/or bone. In another exemplary embodiment, the proximal portion 12 can have a longitudinal length L1 about 75% the total longitudinal length L of the guide pin 10, and the distal portion 14 can have a longitudinal length L2 about 25% of the total longitudinal length L. The longitudinal length L1 of the proximal portion 12 can therefore be about three times the longitudinal length L2 of the distal portion 14. In yet another exemplary embodiment, the longitudinal length L1 of the proximal portion 12 can be less than the longitudinal length L2 of the distal portion 14. In other words, the distal portion 14 can form a majority of the guide pin's total longitudinal length L. Having the distal portion 14 form a majority of the guide pin's total longitudinal length L can allow a greater length of the guide pin 10 to be flexed away from various structures within a patient's body, as discussed below, which can help prevent injury. As a non-limiting example of the distal portion 14 forming the majority of the pin's length L, only the proximal tip 16 of the guide pin 10, e.g., less than about 10% of the pin's total length L, can be formed from a rigid material(s) such that the proximal portion 12 only include the proximal tip 16.

The proximal portion 12 of the guide pin 10 can have a variety of configurations. In an exemplary embodiment, as mentioned above, the proximal portion 12 can be rigid, e.g., can be formed from any one or more rigid materials. The proximal portion 12 can therefore define the longitudinal axis X of the guide pin 10.

The proximal portion 12 of the guide pin 10 can include a penetrating proximal tip 16 configured to penetrate tissue and/or bone, which can facilitate advancement of the guide pin 10 through tissue and/or bone in a proximal direction. The penetrating proximal tip 16 can have a variety of sizes, shapes, and configurations. As in the illustrated embodiment, the penetrating proximal tip 16 can taper proximally to a sharp point, although the penetrating proximal tip 16 can be blunt. In other embodiments, a penetrating proximal tip of a guide pin can include a drill bit, one or more sharpened edges, and/or one or more serrations or teeth. The penetrating proximal tip 16 can cause the proximal end of the guide pin 10 to have a different shape and/or cross-sectional shape than a substantial remainder of the guide pin 10, e.g., a cone shape at the proximal end as opposed to a cylindrical shape in a substantial remainder of the guide pin 10. The penetrating proximal tip 16 can also cause the proximal end of the guide pin 10 to have a different outer diameter than a substantial remainder of the guide pin 10, e.g., by the penetrating proximal tip 16 being proximally tapering.

The distal portion 14 of the guide pin 10 can also have a variety of configurations. In an exemplary embodiment, as mentioned above, the distal portion 14 can be flexible, e.g., can be formed from any one or more flexible materials, such that the distal portion 14 can be configured to flex relative to the proximal portion 12, e.g., bend away from the axis X of the proximal portion 12 at the non-zero angle θ. The angle θ can vary, but, in an exemplary embodiment, the angle can be in a range of about 1 degree to 90 degrees. The distal portion 14 can therefore be configured as a flexible tail.

The distal portion 14 can be formed from any one or more flexible materials configured to allow the distal portion 14 to passively flex, e.g., bend when pressed against one or more adjacent structures such as tissue, another surgical tool, bone, etc. A distal portion 14 configured to passively flex can also be configured to actively flex, e.g., bend in response to an applied force, such as by being manually bent by hand and/or one or more surgical tools. In an exemplary embodiment, as mentioned above, the distal portion 14 can be formed from a shape memory material(s), which can allow the distal portion 14 to passively and actively flex while also allowing the distal portion 14 to be biased to a straight or linear configuration in which the longitudinal axis X2 of the distal portion 14 can be coaxially aligned with the longitudinal axis X of the proximal portion 12. Such a bias can facilitate advancement of the guide pin 10 through tissue and/or bone.

As also mentioned above, the distal portion 14 can be formed from at least one selectively stiffenable material, e.g., shape memory material(s) configured to be activated to change between different states. As will be appreciated by a person skilled in the art, a selectively stiffenable material can be configured to be activated in a variety of ways to change between different states, such as by exposure to different temperatures. One temperature can cause the selectively stiffenable material to have a first stiffness, and another temperature, e.g., a greater temperature, can cause the selectively stiffenable material to have a second, greater stiffness. In an exemplary embodiment, an internal body temperature of a patient can cause the selectively stiffenable material to change from a first stiffness to a second stiffness, or vice versa. Alternatively, a separate internal or external tool can subject the selectively stiffenable material to a temperature to cause a change between the first stiffness and the second stiffness. If the guide pin 10 includes at least one visual indicator, the at least one visual indicator can help indicate where to apply or otherwise expose an increased or decreased temperature to the guide pin 10, e.g., direct a heat element to a dark-color portion of the guide pin 10 instead of to a light-color portion of the guide pin 10. Being formed of a selectively stiffenable material(s) can allow the distal portion 14 to be movable between a first state in which the distal portion 14 has a first stiffness and a second state in which the distal portion 14 has a second stiffness that is greater than, e.g., stiffer than, the first stiffness. In an exemplary embodiment, the first state can be a rigid state, and the second state can be a flexible state such that the distal portion 14 can be configured to change between rigid and flexible states. In this way, the distal portion 14 can be configured to be advanced through tissue and/or bone in the first state to facilitate advancement therethrough and then be changed to the second state in which the distal portion 14 can be passively and/or actively flexed around nearby structures, e.g., delicate tissue such as cartilage. Although in this illustrated embodiment, the distal portion 14 is flexible, e.g., always flexible or configured to be changed to a flexible state, and the proximal portion 12 is rigid, the proximal portion 12 can also be flexible, such as by being formed of a selectively stiffenable material. In this way, the entire guide pin can be configured to be changeable between rigid and flexible states. In use, as discussed further below, only a selected portion of the guide pin, e.g., a distal or trailing portion, can be changed to the flexible state. By being formed of a same material(s), the guide pin can be easier to manufacture and can prevent medical personnel from having to assemble separate proximal and distal portions of a guide pin.

The distal portion 14 can include a suture coupling mechanism configured to engage at least one suture (not shown) to couple the at least one suture to the guide pin 10 such that the at least one suture can trail behind the guide pin 10 when the guide pin 10 is advanced in a proximal direction. The suture coupling mechanism can have a variety of configurations, as will be appreciated by a person skilled in the art, e.g., at least one crimp, at least one opening, etc. In this embodiment, the distal portion 14 includes an eyelet or opening 20 formed therethrough adjacent to a distal tip 18 of the guide pin 10 and having an axis passing therethrough, e.g., into and out of the page as shown in FIG. 1, that can be transverse to the longitudinal axis X of the guide pin 10. The opening 20 can have a length and width sufficient to allow one or more sutures to be threaded therethrough. The suture coupling mechanism can cause the distal end of the guide pin 10 to have a different shape and/or cross-sectional shape than a substantial remainder of the guide pin 10, e.g., an ovular cross-sectional shape at the distal end. The suture coupling mechanism can also cause the distal end of the guide pin 10 to have a different outer diameter than a substantial remainder of the guide pin 10, e.g., by the suture coupling mechanism including a distally tapering crimped end of the guide pin.

The guide pins discussed herein, such as the guide pin 10, can be configured to have one or more cannulated tools, e.g., a scope having a working channel extending therethrough, a reamer, a drill guide, etc., advanced thereover such that the guide pin can guide the one or more cannulated tools into a patient's body. The one or more cannulated tools can be advanced over the guide pin before or after the guide pin is advanced into the patient's body, but in an exemplary embodiment, the guide pin can be at least partially advanced into the patient's body before any cannulated tools are advanced over the guide pin. In other words, the one or more cannulated tools can be configured to overdrill the guide pin 10. The cannulated tools can have a variety of sizes, shapes, and configurations. Generally, the cannulated tool can have an inner passageway, lumen, or channel, generally referred to herein as a "lumen," extending therethrough having a diameter large enough to accommodate passage of the guide wire therethrough. The cannulated tool can have any longitudinal length, e.g., less than a total longitudinal length of the guide pin over which the cannulated tool is advanced so as to allow the guide pin to extend through the cannulated tool's inner passageway to extend out opposed ends thereof. The cannulated tool can be made from any one or more materials, e.g., one or more rigid materials.

FIG. 2 illustrates one embodiment of a cannulated tool configured to be advanced over a guide pin in the form of a cannulated reamer 30. The cannulated reamer 30 can include an elongate tube having a proximal end 32, a distal end 34, and a lumen 36 extending therebetween. A proximal portion of the reamer 30 can have a substantially cylindrical shape with a substantially circular cross-section and a maximum diameter d. The proximal portion of the reamer 30 can have a different shape and/or a different outer diameter than a distal portion of the reamer 30, e.g., by including a cutting element at a distal end 34 thereof. For example, reamer 30 can have a distal cutting head 38 with a maximum diameter $d_2$, as shown in FIG. 2. The diameter $d_2$ of the head 38 can be greater than the diameter d of the reamer's proximal portion, as in the illustrated embodiment. Although the reamer 30 in this illustrated embodiment is an acorn reamer, the reamer can be an elongate member having a different shape and/or different cross-section. For example, FIG. 2A illustrates another exemplary embodiment of a reamer 30A. The reamer 30A can have a substantially constant maximum diameter $d_3$, such as a coring reamer, which can facilitate introduction of the reamer 30A into tissue and/or bone. Although the distal end 34A of reamer 30A in this illustrated embodiment has is flat with jagged teeth, the distal end of the reamer can have a variety of different shapes and/or edges. For example, the edge can be pointed, rounded, or slanted, and the edge of the distal end can be a smooth edge, a cutting edge, or an abrasive edge, for example.

The proximal end 32 of the reamer 30 can include a cutting element, e.g., a serrated edge, a knife blade, a proximal taper, a thread, etc., configured to drill through bone in which the guide pin is inserted so as to form a tunnel through the bone around the guide pin such that the tunnel has a diameter substantially equal to an outer diameter of the reamer 30. An inner diameter of the lumen 36 can vary, but generally it can be greater than a maximum outer diameter of the guide pin advanced therethrough so that the cannulated reamer 30 can pass over and overdrill the guide pin.

The guide pins discussed herein, such as the guide pin 10, and cannulated tools that can be advanced over a guide pin, such as the reamer 30, can each be advanced into a body of a patient, e.g., into tissue and bone of the patient, in a variety of ways. In one embodiment, the guide pin and/or the cannulated tool can be advanced into a patient's body by hand. In another embodiment, one or more surgical tools can be used to advance the guide pin and/or the cannulated tool into the bone. By way of non-limiting example, a mallet can be used to advance the guide pin and/or the cannulated tool into a patient's body. For another non-limiting example, a surgical drill driver can be used to advance the guide pin and/or the cannulated tool into a patient's body. Generally, the surgical drill driver can include a chuck configured to place a guide pin within a patient's body, such as through a trigger system. Surgical drill drivers can have a variety of configurations, as will be appreciated by a person skilled in the art, and are available from a variety of manufacturers. Non-limiting examples of drill drivers include MPOWER™ powered instruments, e.g., PRO6202 Dual Trigger Full Function Modular Handpiece with a PRO6228 Wire Driver, available from ConMed Linvatec of Largo, Fla.; Cordless Driver small bone battery power instruments, e.g., Cordless Driver 2 Surgical Drill, available from Stryker Corp. of Kalamazoo, Mich.; and Anspach drills available from Synthes, Inc. of West Chester, Pa.

Any of the guide pins discussed herein can be provided as part of a kit including a plurality of sutures each configured to be coupled to the guide pin via a suture coupling mechanism of the guide pin. In this way, the suture(s) having the most appropriate size and strength for use in a particular surgical procedure with a particular patient can be selected for use from the kit. Similarly, any of the guide pins discussed herein can be provided as part of a kit including a plurality of different guide pins varying in one or more ways, e.g., longitudinal length, maximum diameter, flexibility, etc., such that one of the guide pins can be selected for use from the kit in accordance with a particular surgical procedure and/or a particular patient. The kit including the plurality of different guide pins can also include a plurality of different sutures. Further, any of the guide pins discussed herein can be included in a kit including at least one cannulated tool configured to be advanced over the guide pin and/or at least one driver tool configured to drive the guide pin into bone. The kit including the at least one cannulated tool and/or at least one driver tool can also include one or more sutures and/or one or more different guide pins.

The guide pins discussed herein can be used in a variety of surgical procedures in which a guide pin can be used to facilitate insertion of a surgical device into a patient's body over the guide pin, such as a procedure for attaching tissue to bone, e.g., ACL repair, rotator cuff repair, etc. In an exemplary embodiment, a procedure including passage of the guide pin into a patient's body can be a minimally invasive procedure, but as will be appreciated by a person skilled in the art, the guide pins discussed herein also have application in open surgical instrumentation as well as application in robotic-assisted surgery.

FIGS. 3-6 illustrate an exemplary embodiment of a surgical procedure that includes advancing a guide pin 610 into a body of a patient. While FIGS. 3-6 show the guide pin 610 being advanced into a knee of a patient in a context of ACL repair, the methods and devices disclosed herein can be used in a variety of medical procedures in which a guide pin is advanced into a patient's body, as mentioned above. Additionally, although this exemplary embodiment is discussed with reference to the guide pin 610 shown in FIGS. 3-5, any of the guide pins discussed herein can be advanced into a patient's body in this or other ways.

The surgical procedure can include preparing the patient for surgery using standard techniques. In a minimally invasive procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body.

Figure 3:
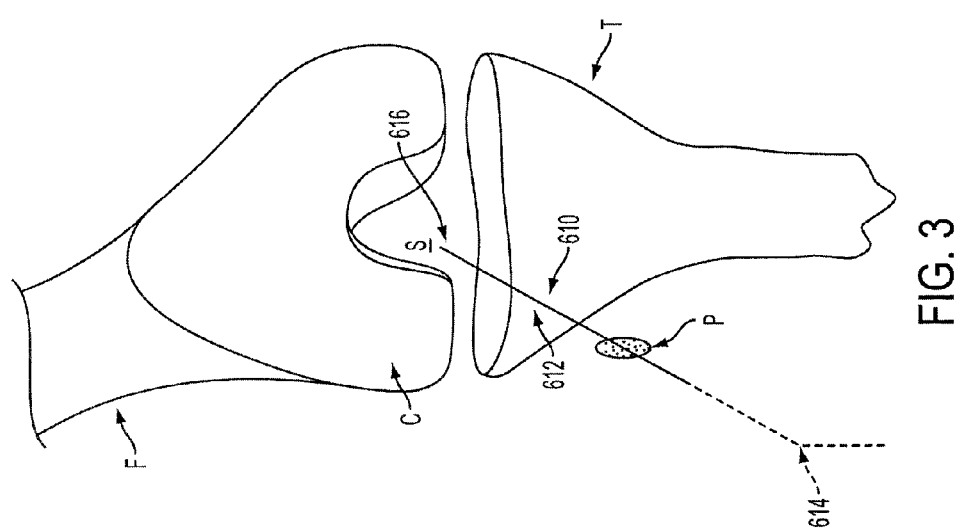
FIG. 3 is a perspective view of another embodiment of a guide pin being advanced into intra-articular space within a knee.
Figure 8:
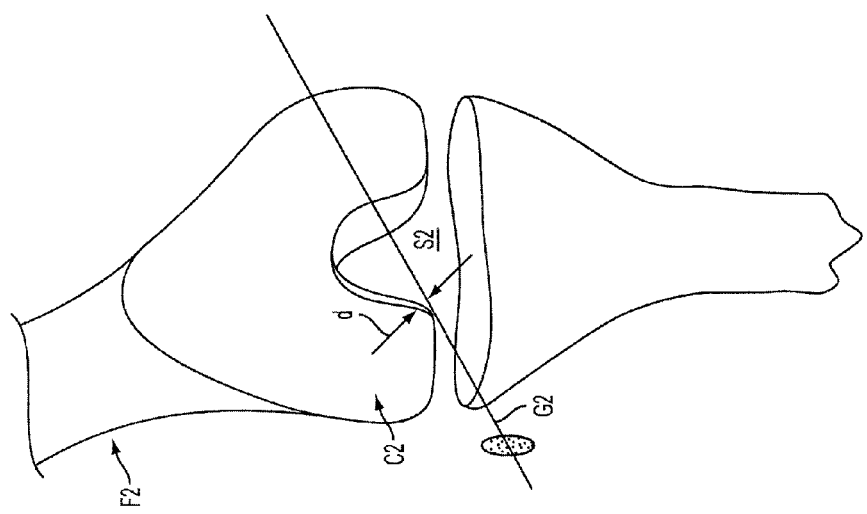
FIG. 8 is a perspective view of a prior art guide pin being advanced into a knee with an anteriomedial approach.

As shown in FIG. 3, a proximal end 612 of the guide pin 610 can be advanced proximally through an anteromedial portal P formed through the skin of the patient. The portal P can be formed in a variety of ways, as will be appreciated by a person skilled in the art, such as by nicking or cutting the skin with a cutting instruments such as a knife, by inserting a proximal tip 616 of the guide pin 610 directly therethrough, etc. The proximal tip 616 in this illustrated embodiment has a blunt, non-tapered end. The guide pin 610 can be advanced through the portal P in a variety of ways, as discussed above, such as by being coupled to a drill chuck and drilled into the patient to form a path therethrough. In some embodiment, the path can be pre-formed through the patient, such as with a drill. Although the portal P includes an anteromedial portal P in the illustrated embodiment, the location of the portal can vary. In an exemplary embodiment, the portal P can be formed for an anteromedial approach into a femur F of the patient, e.g., below the femur F and adjacent a tibia T of the patient. In this way, the guide pin 610 can be advanced into an intra-articular space S located within the patient between the femur F and the tibia T without first passing through the tibia T, as opposed to a traditional transtibial approach, an embodiment of which is illustrated in FIG. 7 in which a guide pin G1 is advanced through a tibial tunnel U1 formed in a tibia T1 prior to advancing into a femur F1. The portal can, however, be formed through a tibia if, e.g., a graft is desired to be secured in the tibia and in the femur. Referring again to the embodiment of FIGS. 3-6, the patient's knee can be flexed prior to advancing the guide pin 610 into the intra-articular space S. The guide pin 610 can therefore approach the intra-articular space S at various angles, such as at a more oblique angle than in a traditional anteromedial approach, an embodiment of which is illustrated in FIG. 8 in which a guide pin G2 is advanced into a femur F2. Although a distal portion 614 of the guide pin 610 is shown in a flexed or bent configuration in FIG. 3 prior to being advanced into the patient, e.g., such that a longitudinal axis X3 of the proximal portion 612 is angularly offset from a longitudinal axis X4 of the distal portion 614, the distal portion 614 can be in the flexed or bent configuration or in a straight or linear configuration prior to, during, or after it is advanced into a patient.

Figure 4:
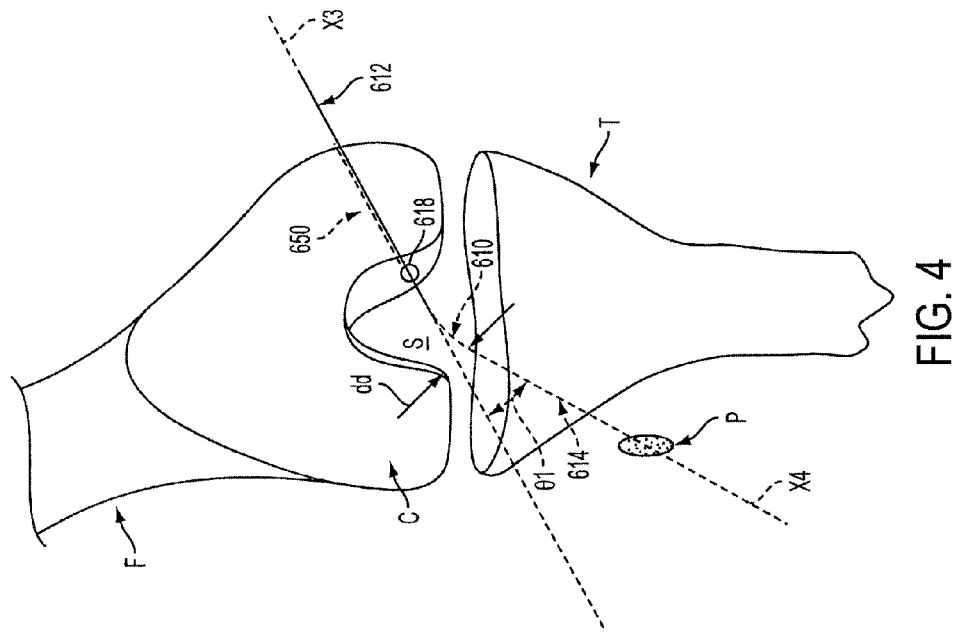
FIG. 4 is a perspective view of the guide pin of FIG. 3 further advanced proximally into the knee.

As shown in FIG. 4, the proximal portion 612 of the guide pin 610 can be advanced proximally from within the intra-articular space S and into the femur F. Any longitudinal length of the proximal portion 612 can be advanced into the femur F. In an exemplary embodiment, the proximal portion 612 can be advanced into the femur F until the proximal tip 616 thereof protrudes through a lateral side of the knee, as shown in FIG. 4. However, in another embodiment, a guide pin can be advanced only partially through bone so as to be positioned therein for formation of a blind tunnel. The proximal portion 612 of the guide pin 610 can continue to be advanced through the femur F until the distal portion 614 of the guide pin 610 enters the intra-articular space S, with a proximal end of the distal portion 614 being positioned within the intra-articular space S and with a partial longitudinal length of the distal portion 614 extending medially through the portal P, as also shown in FIG. 4. In other words, the distal portion 614 of the guide pin 610 can be positioned outside the femur F and medial to an entrance 618 of the proximal portion 612 of the guide pin 610 into the femur F. With the distal portion 614 positioned across the intra-articular space S, the distal portion 614 can be flexed or bent within the intra-articular space S such that the longitudinal axis X4 of the distal portion 614 extends at a non-zero angle θ1 relative to the longitudinal axis X3 of the proximal portion 612. The portal P can have adequate mobility through skin and tissue to allow the distal portion 614 of the guide pin 610 to be flexed or bent while being positioned through the portal P and positioned within the patient's body.

The distal portion 614 can be radially flexed or bent within the intra-articular space S in one direction relative to the longitudinal axis X3 of the proximal portion 612 such that a longitudinal axis X4 of the distal portion 614 can extend substantially linearly or straight as shown in FIG. 4, or the longitudinal axis X4 of the distal portion 614 can be radially flexed or bent in a plurality of direction relative to the longitudinal axis X3 of the proximal portion 612 such that the longitudinal axis X4 of the distal portion 614 can extend non-linearly at a plurality of angles relative to the longitudinal axis X3 of the proximal portion 612. In an exemplary embodiment, the distal portion 614 can be bent in a direction away from articular cartilage C facing the intra-articular space S, thereby adjusting a distance dd between the intra-articular cartilage C and the guide pin 610, e.g., between the intra-articular cartilage C and a point along the distal portion 614 of the guide pin 610 that is closest to the intra-articular cartilage C. The distance dd can be adjusted such that the distance dd is maintained at a constant amount or, in an exemplary embodiment, such that the distance dd is increased. Once the guide pin 610 passes the articular cartilage C, the distal portion 614 of the guide pin 610 can be bent or flexed again, e.g., so as to align its axis X4 with the axis X3 of the proximal portion so as to be at a zero angle θ1 relative thereto. By allowing the distance dd between the intra-articular cartilage C and the guide pin 610 to be adjusted, the guide pin 610, as well as any one or more cannulated tools inserted thereover, such as an acorn reamer having an enlarged head, e.g., the reamer 30 of FIG. 2, can be less likely to scrape, tear, contact, and/or otherwise adversely affect the delicate cartilage C. In contrast, in the traditional anteromedial approach shown in FIG. 8, a distance d between the guide pin G2 within intra-articular space S2 and articular cartilage C2 facing the intra-articular space S2 is non-adjustably fixed and is less than the distance dd at which the guide pin 610 of FIG. 4 can be adjusted away from the intra-articular cartilage C.

If the distal portion 614 includes a selectively stiffenable material, the selectively stiffenable material can be activated before flexing or bending the distal portion 614 to allow the distal portion 614 to be so flexed or bent. The selectively stiffenable material can be activated again after flexing or bending the distal portion 614, which can fix the distal portion 614 at the distance dd from the cartilage C.

Figure 5:
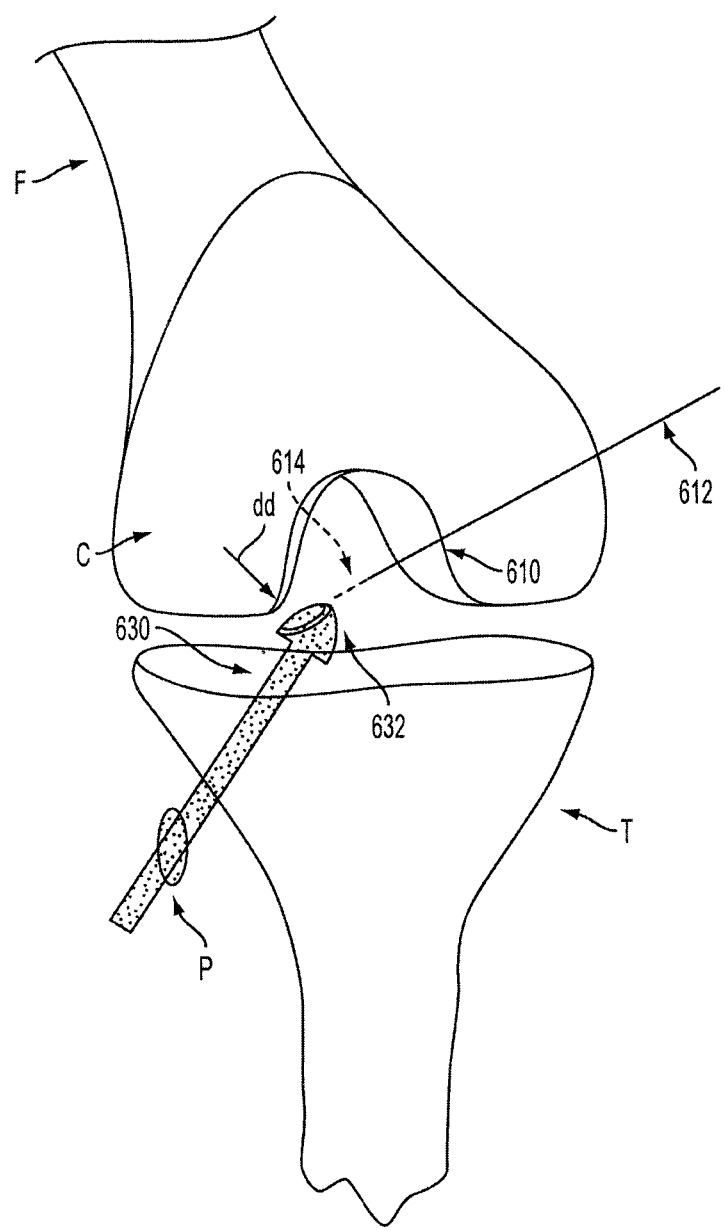
FIG. 5 is a perspective view of the guide pin of FIG. 4 having an embodiment of a cannulated tool inserted thereover and forming a femoral tunnel.

As shown in FIG. 5, a proximal end of a cannulated tool, e.g., a proximal end 632 of an acorn reamer 630, can be advanced over the distal portion 614 of the guide pin 610 and advanced towards the proximal portion 612. The reamer 630 can be advanced through the portal P and over the guide pin 610 in a variety of ways, as discussed above, such as by being coupled to a drill chuck and drilled into the patient.

In an exemplary embodiment, the proximal end 632 of the reamer 630 can be advanced over the guide pin 610 simultaneously with and/or after the distal portion 614 has been bent or flexed, which can help ensure that the distance dd is large enough to reduce chances of the reamer 610 scraping, tearing, contacting, and/or otherwise adversely affecting the delicate cartilage C. Repeatedly adjusting the distance dd as the reamer 630 advances over the guide pin 610 can help ensure the distance dd at an optimal amount. Alternatively, the proximal end 632 of the reamer 630 can be advanced over the guide pin 610 prior to such bending or flexing, although the reamer 630 can be located outside the portal P, e.g., outside the patient, until after the distal portion 614 is flexed, which can facilitate maneuverability of the distal portion 614.

The reamer 630 can be advanced over the guide pin 610 through the intra-articular space S such that the proximal end 632 of the reamer 630 contacts the femur F at the entrance 618 and advances into the femur F over the proximal portion 612 of the guide pin 610 such that the reamer 630 overdrills the proximal portion 612 of the guide pin 610, creating a femoral tunnel 650. The reamer 630 can be advanced any amount through the femur F to form any length femoral tunnel 650, but in an exemplary embodiment, as shown in FIG. 6, the femoral tunnel 650 can extend through the lateral side of the femur F so as to have two open ends.

Figure 6:
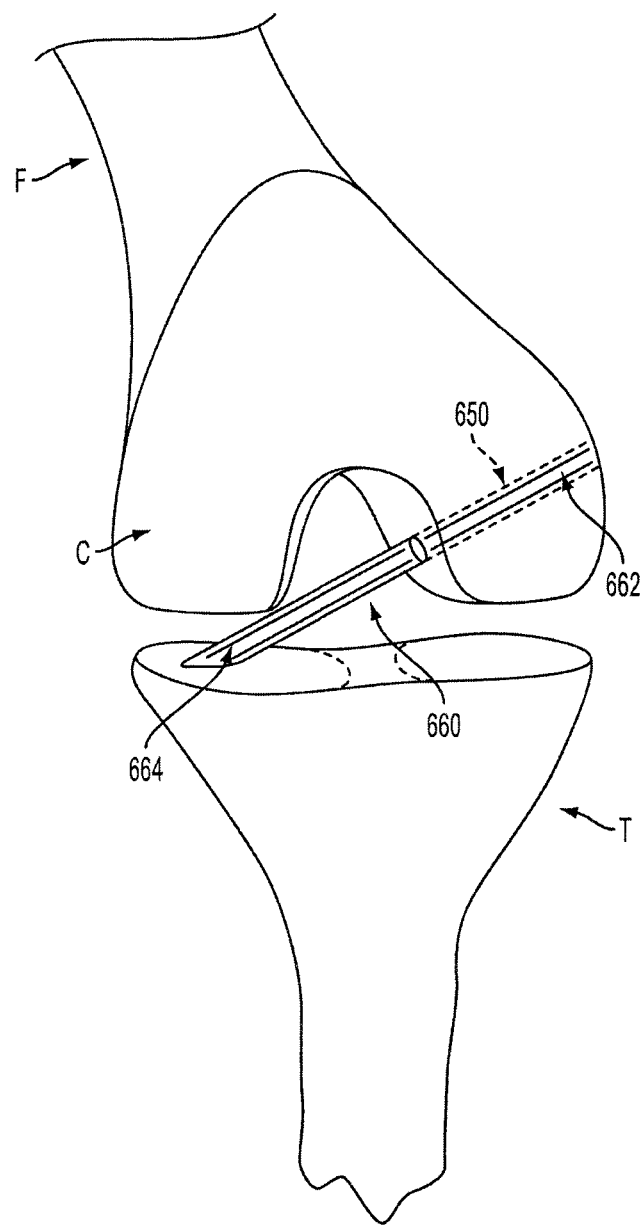
FIG. 6 is a perspective view of the femoral tunnel of FIG. 5 having a ligament graft positioned therein.
Figure 7:
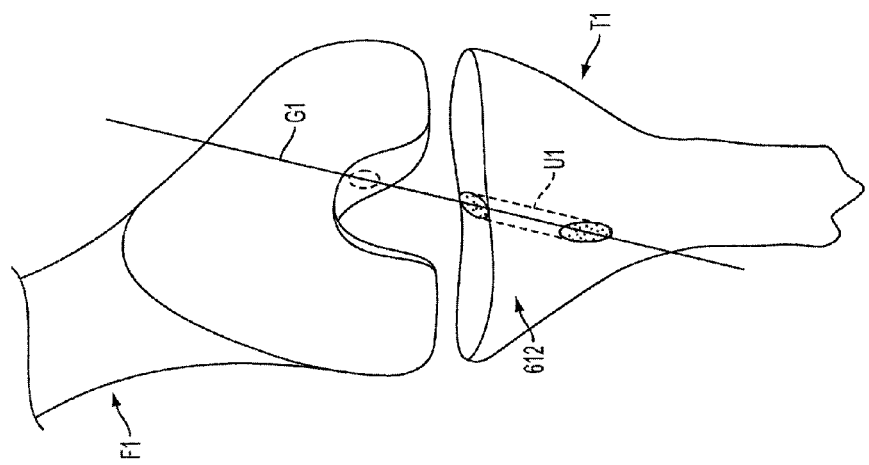
FIG. 7 is a perspective view of a prior art guide pin being advanced into a knee with a transtibial approach.

As shown in FIG. 6, once the femoral tunnel 650 is formed, a ligament graft 660 can be positioned therein. To provide space for the ligament within the femoral tunnel 650, the guide pin 610 and the reamer 630 can be removed from the femoral tunnel 650, e.g., by pulling the reamer 630 distally through the portal P and pushing the guide pin 610 proximally to push the guide pin 610 through the lateral side of the femur F. Alternatively, both the reamer 630 and the guide pin 610 can exit the femoral tunnel 650 through a same side thereof. In an exemplary embodiment, the ligament graft 660 can be attached in any way to at least one suture (not shown) coupled to a suture coupling mechanism (not shown) at a distal end of the distal portion 614 of the guide pin 610. Thus, when the guide pin 610 advances in a proximal direction through the femoral tunnel 650, the graft can trail the guide pin 610 and enter the femoral tunnel 650. Depending on a length of the suture, a size of the graft 660, a length of the pin 610, and the length of the femoral tunnel, the guide pin 610 can be completely removed from the femoral tunnel 650 prior to the graft 660 entering the tunnel 650, or alternatively the guide pin 610 can be partially removed from the lateral side of the femoral tunnel 650 as the graft 660 enters the femoral tunnel 650. The ligament graft 660 can thus be positioned within the femoral tunnel 650 and be attached to the femur F in any way, e.g., adhesive, an anchor, etc. The ligament graft 660 can alternatively or additionally be attached to the tibia T in any way, e.g., adhesive, an anchor, etc., that can be the same or different than how the ligament graft 660 is attached to the femur F. In the illustrated embodiment, a proximal end 662 of the graft 660 can be attached to the femur F, and a distal end 664 of the graft 660 can be attached to the tibia T. A tibial tunnel can be formed through the tibia T to facilitate securing the graft 660 to the tibia T. The tibial tunnel can be formed in any number of ways, as will be appreciated by a person skilled in the art.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   advancing a rigid proximal portion of a guide pin through a tissue opening adjacent to a femur, across an intra-articular space, and into a femoral tunnel such that a flexible distal portion of the guide pin extends across the intra-articular space and extends out of the tissue opening;
   bending the flexible distal portion of the guide pin within the intra-articular space such that the rigid proximal portion of the guide pin extends at a non-zero angle relative to the flexible distal portion;
   advancing a cannulated reamer over the flexible distal portions of the guide pin to position a proximal tip of the reamer in contact with the femur, the cannulated reamer being manipulated to substantially avoid contact with articular cartilage within the intra-articular space;
   advancing the cannulated reamer over the rigid proximal portion of the guide pin within the femoral tunnel; and
   after advancing the cannulated reamer over the flexible distal portion of the guide pin, straightening the flexible distal portion of the guide pin and reaming the cannulated reamer into the femur over the rigid proximal portion of the guide pin.

2. The method of claim 1, wherein bending the flexible distal portion of the guide pin comprises bending the flexible distal portion of the guide pin within the intra-articular space away from the articular cartilage.

3. The method of claim 1, wherein advancing the rigid proximal portion of the guide pin through the femur comprises advancing the rigid proximal portion of the guide pin to protrude through a lateral side of the femur.

4. The method of claim 1, wherein the rigid proximal portion and the flexible distal portion are integrally formed.

5. The method of claim 1, wherein bending the flexible distal portion of the guide pin within the intra-articular space adjusts a distance between the flexible distal portion of the guide pin and femoral articular cartilage.

6. The method of claim 5, wherein adjusting the distance between the flexible distal portion of the guide pin and the femoral articular cartilage comprises increasing the distance.

7. The method of claim 1, further comprising removing the guide pin and the reamer from a tunnel formed in the femur by the reamer;
   after removing the guide pin and the reamer, advancing a graft into the tunnel; and
   securing the graft within the tunnel.

8. The method of claim 1, wherein when the proximal portion of the guide pin is advanced through the tissue opening and across the intra-articular space, the distal portion of the guide pin is flexible.

9. The method of claim 1, wherein the flexible distal portion of the guide pin is positioned entirely outside the femur when the flexible distal portion of the guide pin is bent and when the cannulated reamer is advanced over the rigid proximal portion of the guide pin within the femoral tunnel.

10. The method of claim 1, wherein a longitudinal length of the rigid proximal portion forms at least half a total longitudinal length of the guide pin.

11. The method of claim 1, wherein an outer diameter of the guide pin has a substantially constant outer diameter along the rigid proximal portion and the flexible distal portion.

12. The method of claim 1, wherein an outer diameter of the guide pin has a substantially constant outer diameter along the rigid proximal portion and the flexible distal portion except at a tapering proximal tip of the rigid proximal portion.

13. A surgical method, comprising:
   advancing a rigid proximal portion of a guide pin through a tissue opening adjacent to a femur, across an intra-articular space and into a femoral tunnel such that a flexible distal portion of the guide pin extends across the ultra-articular space and extends out of the tissue opening, wherein when the proximal portion of the guide pin is advanced through the tissue opening and across the intra-articular space, the distal portion of the guide pin is rigid;
   bending the flexible distal portion of the guide pin within the intra-articular space such that the rigid proximal portion of the guide pin extends at a non-zero angle relative to the flexible distal portion;
   advancing a cannulated reamer over the flexible distal portion of the guide pin to position a proximal tip of the reamer in contact with the femur, the cannulated reamer being manipulated to substantially avoid contact with articular cartilage within the intra-articular space;
   advancing the cannulated reamer over the rigid proximal portion of the guide pin within the femoral tunnel; and
   activating a selectively stiffenable material forming at least a portion of the guide pin to make the distal portion of the guide pin flexible.

14. The method of claim 13, wherein the rigid proximal portion of the guide pin remains rigid when the selectively stiffenable material is activated.

* * * * *